US008963095B2

(12) United States Patent
Li (10) Patent No.: US 8,963,095 B2
(45) Date of Patent: Feb. 24, 2015

(54) ELECTROKINETIC MICROFLUIDIC FLOW CYTOMETER APPARATUSES WITH DIFFERENTIAL RESISTIVE PARTICLE COUNTING AND OPTICAL SORTING

(71) Applicant: Diagnostic Chips, LLC, Burlington, NC (US)

(72) Inventor: Dongqing Li, Waterloo (CA)

(73) Assignee: Diagnostic Chips, LLC, Burlington, NC (US)

( * ) Notice: Subject to any disclaimer, the term of this patent is extended or adjusted under 35 U.S.C. 154(b) by 0 days.

(21) Appl. No.: 14/089,816

(22) Filed: Nov. 26, 2013

(65) Prior Publication Data

US 2014/0273193 A1 Sep. 18, 2014

Related U.S. Application Data

(60) Provisional application No. 61/730,281, filed on Nov. 27, 2012.

(51) Int. Cl.
*G01T 1/20* (2006.01)
*G01N 15/14* (2006.01)
*G01N 15/10* (2006.01)
*B01L 3/00* (2006.01)

(52) U.S. Cl.
CPC ........ *G01N 15/1404* (2013.01); *G01N 15/1031* (2013.01); *B01L 3/50273* (2013.01); *G01N 15/1056* (2013.01); *G01N 15/1484* (2013.01); *G01N 2015/1415* (2013.01); *G01N 2015/1081* (2013.01); *G01N 2015/149* (2013.01)
USPC ........................................................ 250/364

(58) Field of Classification Search
CPC .......... G01N 15/1484; G01N 15/1031; G01N 15/1056
USPC ........................................................ 250/354
See application file for complete search history.

(56) References Cited

U.S. PATENT DOCUMENTS

| 6,337,740 | B1 | 1/2002 | Parce | |
|---|---|---|---|---|
| 6,613,512 | B1 | 9/2003 | Kopf-Sill et al. | |
| 7,306,924 | B2 | 12/2007 | Gomez et al. | |
| 7,312,085 | B2 * | 12/2007 | Chou et al. | 436/43 |
| 7,452,726 | B2 * | 11/2008 | Chou et al. | 436/63 |
| 7,488,451 | B2 * | 2/2009 | Zarowitz et al. | 422/67 |
| 7,569,382 | B2 | 8/2009 | Li | |

(Continued)

OTHER PUBLICATIONS

Chabinyc et al., "An Integrated Fluorescence Detection System in Poly(dimethylsiloxane) for Microfluidic Applications", *Analytical Chemistry*, 2001, 73:4491-4498.

(Continued)

*Primary Examiner* — Kiho Kim
(74) *Attorney, Agent, or Firm* — Myers Bigel Sibley & Sajovec, P.A.

(57) ABSTRACT

The present invention provides electrokinetic microfluidic cytometers useful for detecting and/or sorting fluid-borne particles. In some embodiments, the electrokinetic microfluidic flow cytometer apparatus comprises a substrate having a microchannel formed therein, a particle-sensing gate that reduces the cross-sectional area of a portion of the microchannel, a pair of signal- and noise-detection electrodes, and a particle-detection circuit that is electrically connected to the signal- and noise-detection electrodes and is configured to generate a particle-detection signal responsive to differences in resistivity across the particle-sensing gate.

26 Claims, 5 Drawing Sheets

(56) References Cited

U.S. PATENT DOCUMENTS

| | | | |
|---|---|---|---|
| 8,188,438 B2 | 5/2012 | Li | |
| 2004/0233424 A1* | 11/2004 | Lee et al. | 356/246 |
| 2005/0148064 A1 | 7/2005 | Yamakawa et al. | |
| 2005/0191620 A1 | 9/2005 | McDevitt et al. | |
| 2006/0081954 A1* | 4/2006 | Tondra et al. | 257/421 |
| 2008/0003142 A1 | 1/2008 | Link et al. | |
| 2008/0070311 A1 | 3/2008 | Li | |
| 2008/0213821 A1 | 9/2008 | Liu et al. | |
| 2009/0302228 A1* | 12/2009 | Hadjioannou et al. | 250/370.08 |
| 2010/0136544 A1 | 6/2010 | Agresti et al. | |
| 2011/0027913 A1* | 2/2011 | Bau et al. | 436/518 |
| 2013/0086980 A1* | 4/2013 | Gadini et al. | 73/61.71 |

OTHER PUBLICATIONS

Cui et al., "Optical particle detection integrated in a dielectrophoretic lab-on-a chip", *Journal of Micromechanics and Microengineering*, 2002, 12:7-12.

Fu et al., "Electrokinetically driven micro flow cytometers with integrated fiber optics for on-line cell/particle detection", *Analytica Chimica Acta*, 2004, 507:163-169.

Fu et al., "Multiple volume injection technique for high-resolution DNA sample detection utilizing planar microfluidic chip", *Proceedings of the 26th Annual International Conference of the IEEE EMBS*, 2004, San Francisco, CA, USA, pp. 5017-5020.

International Search Report and the Written Opinion of the International Search Authority Corresponding to International Application No. PCT/US2010/050620; Date of Mailing: Nov. 22, 2010.

Lee et al., "Micro flow cytometers with buried SU-8/SOG optical waveguides" *Sensors and Actuators A*, 2003, 103:165-170.

Mogensen et al., "Integration of polymer waveguides for optical detection in microfabricated chemical analysis systems" *Applied Optics*, 2003, 42(19):4072-4079.

Rodriguez et al., "A Microchip CD$ Counting Method for HIV Monitoring in Resource-Poor Settings", *PLoS Medicine*, 2005, 2(7):0663-0672.

Tung et al., "PDMS based opto-fluidic micro flow cytometer with two-color, multi-angle fluorescence detection capability using PIN photodiodes", *Sensors and Actuators B*, 2004, 98:356-367.

Xiang et al., "Multi-Functional Particle Detection with Embedded Optical Fibers in a Poly(dimethylsiloxane) Chip", *Instrumentation Science and Technology*, 2005, 33:597-607.

Xu et al., "Fabrication and testing investigation of low-voltage integrated electrophoresis chip based on silicon-on-insulator-MEMS", *Journal of Micro/Nanolithography*, 2007, 6(3): 033009-1-03009-7.

Zahow et al., "Guided microfluidics by electromagnetic capillary focusing", *Applied Physics Letters*, 2002, 80(8): 1483-1486.

Zhang et al., "Methods for counting particles in microfluidic applications", *Microfluid Nanofluid*, 2009, 7:739-749.

\* cited by examiner

ELECTROKINETIC MICROFLUIDIC FLOW CYTOMETER APPARATUSES WITH DIFFERENTIAL RESISTIVE PARTICLE COUNTING AND OPTICAL SORTING

CROSS-REFERENCE TO RELATED APPLICATIONS

This application claims the benefit of priority under 35 U.S.C. §119(e) to U.S. Provisional Patent Application No. 61/730,281, filed on Nov. 27, 2012, the disclosure of which is incorporated herein by reference in its entirety.

FIELD OF THE INVENTION

The present invention generally relates to the field of microfluidics, and more particularly to microfluidic flow cytometers and uses thereof.

BACKGROUND

Flow cytometry provides a method of detecting and analyzing cells or particles contained in a sample, for example, blood cells in blood such as red blood cells (erythrocytes), white blood cells (leukocytes) and blood platelets (thrombocytes), or material components in urine such as bacteria, blood cells, epithelial cells or casts. These cells or material components may increase or decrease in number responsive to onset or progression of a disease. Accordingly, a disease can be diagnosed by detecting the status of each cell or material component on the basis of information about granules or particles in the sample.

Flow cytometer measures the number of cells and detects the number of a specific type of cells by optical processes such, as light scattering and fluorescence measurement, as the cells travel in suspension one by one passing a sensing point. Some flow cytometers from well-known vendors such as Beckman-Coulter or Becton Dickenson are expensive, with the cost ranging from $75,000-$125,000 which limits their availability to large reference laboratories. In addition to the initial cost of the instrument, service contracts for these instruments are typically 10% of the cost of the instrument on an annual basis. In addition, the sample volumes are usually large, such as in the 100 microliter range, and the necessary reagent volumes are correspondingly expensive.

For example, in the field of HIV treatments, an important parameter for determining disease staging is the number of CD4+ T cells (unit of cells/mm$^3$) in peripheral blood. However, the laboratory evaluation of CD4+ T cell numbers can be cumbersome and expensive. Typically, the total lymphocyte count is determined by a routine CBC (complete blood count) assay, the percentage of CD4+ T lymphocytes as a function of total lymphocytes is determined by flow cytometry, and these values are multiplied to determine an absolute CD4+ T cell number. This analysis is expensive, time consuming and generally not locally available for less wealthy regions of the United States and the world.

Many clinical applications require frequent blood tests to monitor patients' status and the therapy effectiveness. It is highly desirable to use only small volume blood samples from patients for each test. Furthermore, it is highly desirable to have affordable and portable flow cytometry instruments for field applications, point-of-care applications and applications in resource-limited locations. Recently, efforts have been made to apply microfluidic technologies to flow cytometric analysis of cells to attempt to manufacture small, portable flow cytometers.

SUMMARY OF EMBODIMENTS OF THE INVENTION

A first aspect of the present invention is an electrokinetic microfluidic flow cytometer (hereinafter "EMFC") apparatus comprising a substrate, a particle-sensing gate that reduces the cross-sectional area of a portion of the microchannel, a pair of signal- and noise-detection electrodes and a particle-detection circuit. The substrate comprises an input port, an output port and a microchannel that connects the input port and the output port to allow a particle-carrying fluid to flow from the input port to the output port. Each of the signal- and noise-detection electrodes is mounted in/on a surface of the microchannel (e.g., in/on a sidewall of the microchannel), with one signal- and noise-detection electrode positioned upstream of the particle-sensing gate and the other signal- and noise-detection electrode positioned downstream of the particle-sensing gate. The particle-detection circuit is electrically connected to the signal- and noise-detection electrodes and is configured to generate a particle-detection signal responsive to a differential voltage across the signal- and noise-detection electrodes, wherein the differential voltage across the signal- and noise-detection electrodes tracks changes in resistivity across the particle-sensing gate as particles in the particle-carrying fluid pass through the particle-sensing gate. The particle-detection circuit is configured to at least substantially cancel a common component of ambient electrical noise received by the signal- and noise-detection electrodes.

Electroosmotic flow between the input port and the output port may be generated by creating an electric field along the microchannel, thereby creating an electrokinetic force to transport fluid from the input port to the output port. As will be understood by those skilled in the art, such an electrokinetic force may be generated by applying a voltage across an electrode positioned within the input port and an electrode positioned within the output port.

In some embodiments, the EMFC apparatus further comprises a particle-counting circuit configured to count individual particles as they pass through the particle-sensing gate.

In some embodiments, the EMFC apparatus further comprises an optical-characterization apparatus configured to detect one or more optical characteristics of particles as they pass through an optical-detection region of the microchannel. In some such embodiments, the optical-characterization apparatus comprises a primary photodetector configured to detect light emitted by particles as they pass through the optical-detection region of the microchannel and to generate an output signal responsive thereto, a reference photodetector configured to generate a reference noise signal that is not responsive to light emitted by particles as they pass through the optical-detection region of the microchannel and that is characteristic of the noise component in the output signal, and a comparator circuit configured to generate a particle-characterization signal responsive to a difference between the output signal and the reference noise signal so that the particle-characterization signal is at least substantially free of the noise component from the output signal.

In some embodiments, the output port comprises a plurality of particle-sorting output ports, and the EMFC apparatus further comprises a particle-sorting apparatus configured to sort particles responsive to one or more optical characteristics thereof. In some such embodiments, the particle-sorting apparatus comprises a particle-sorting circuit configured to separately and selectively control the electroosmotic flow between the optical-detection region of the microchannel and each of the particle-sorting output ports such that individual particles may be selectively transported to one of the particle-sorting outputs responsive to the optical characteristic(s) detected by the optical-characterization apparatus.

A second aspect of the present inventions is an EMFC apparatus comprising a substrate, a light source, a first primary photodetector, a second primary photodetector, a reference photodetector, a first comparator circuit and a second comparator circuit. The substrate comprises an input port, a plurality of particle-sorting output ports and a microchannel that fluidly connects the input port and the plurality of particle-sorting output ports to allow a particle-carrying fluid to flow from the input port to the plurality of particle-sorting output ports. The light source is configured to emit one or more wavelengths of light to illuminate an optical-detection region of the microchannel. The first primary photodetector is positioned above the substrate and is configured to detect a first wavelength light emitted by particles as they pass through the optical-detection region of the microchannel and to generate a first output signal responsive thereto. The second primary photodetector is positioned beneath the substrate and is configured to detect a second wavelength of light emitted by particles as they pass through the optical-detection region of the microchannel and to generate a second output signal responsive thereto. The reference photodetector is configured to generate a reference noise signal that is not responsive to light emitted by particles as they pass through the optical-detection region of the microchannel and that is characteristic of noise components in the first and second output signals. The first comparator circuit is configured to generate a first particle-characterization signal responsive to a difference between the first output signal and the reference noise signal so that the first particle-characterization signal is at least substantially free of the noise component from the first output signal. The second comparator circuit is configured to generate a second particle-characterization signal responsive to a difference between the second output signal and the reference noise signal so that the second particle-characterization signal is at least substantially free of the noise component from the second output signal.

In some embodiments, the first and second comparator circuits each comprise a differential amplifier having a pair of input terminals, wherein one of the input terminals of the first differential amplifier is configured to receive the first output signal from the first primary photodetector and the other input terminal of the first differential amplifier is configured to receive the reference noise signal from the reference photodetector, wherein one of the input terminals of the second differential amplifier is configured to receive the second output signal from the first primary photodetector and the other input terminal of the second differential amplifier is configured to receive the reference noise signal from the reference photodetector, and wherein each differential amplifier is configured to generate its particle-characterization signal responsive to a voltage difference between its two input terminals.

In some embodiments, the EMFC apparatus further comprises a control circuit configured to classify particles responsive to the particle-characterization signals.

In some embodiments, the EMFC apparatus further comprises a particle-sorting circuit configured to separately and selectively control the electroosmotic flow between the optical-detection region of the microchannel and each of the particle-sorting output ports such that individual particles may be selectively transported to one of the particle-sorting outputs responsive to the particle-characterization signal. In some such embodiments, the particle-containing fluid comprises at least two types of blood cell and the particle-sorting circuit is configured to separately and selectively control voltages applied between the optical-detection region of the microchannel and the particle-sorting output ports such that a first type of blood cell is transported to one of the particle-sorting outputs and a second type of blood cell is transported to one other of the particle-sorting outputs.

The foregoing and other objects and aspects of the present invention are explained in greater detail in the drawings herein and the specification set forth below.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The drawings are not necessarily drawn to actual or relative scale, emphasis instead being placed upon illustrating certain aspects of the present invention. Like numbers refer to like elements throughout.

DETAILED DESCRIPTION OF EMBODIMENTS OF THE INVENTION

The present invention is explained in greater detail below. This description is not intended to be a detailed catalog of all the different ways in which the invention may be implemented or of all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention, and not to exhaustively specify all permutations, combinations and variations thereof.

All patents, patent publications, non-patent publications referenced herein are incorporated by reference in their entireties for all purposes and to the same extent as if each was specifically and individually indicated to be incorporated by reference.

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Although the following terms are believed to be well understood by those skilled in the art, the following definitions are set forth to facilitate understanding of the presently disclosed subject matter.

As used herein, the singular forms "a", "an" and "the" are intended to include the plural forms as well, unless the context clearly indicates otherwise.

As used herein, the term "about," when used in reference to a measurable value such as length, width and the like, refers to a variation of 0.1%, 0.25%, 0.5%, 0.75%, 1%, 2%, 3%, 4%, 5%, 6,%, 7%, 8%, 9%, 10%, 15% or even 20% of the specified amount. Thus, if a given parameter is described as "about 50 µm," it is to be understood that, in some embodiments, the parameter is 50 µm whilst in other embodiments it may be anywhere from 40 to 60 µm (i.e., 50±10 µm).

As used herein, the term "and/or" refers to and encompasses any and all possible combinations of one or more of the associated listed items, as well as the lack of combinations when interpreted in the alternative ("or").

As used herein, the terms "comprise," "comprises," "comprising," "include," "includes" and "including" specify the presence of stated features, integers, steps, operations, elements, and/or components, but do not preclude the presence or addition of one or more other features, integers, steps, operations, elements, components, and/or groups thereof.

As used herein, the term "consists essentially of" (and grammatical variants thereof), as applied to the apparatuses and methods of the present invention, means that the apparatuses/methods may contain additional components/steps so long as the additional components/steps do not materially alter the apparatus/method. The term "materially alter," as applied to an apparatus/method of the present invention, refers to an increase or decrease in one or more characteristics of the apparatus/method of at least about 20% or more. For example, a component added to an apparatus of the present invention may be deemed to "materially alter" the apparatus if it increases or decreases the sensitivity of the apparatus by at least 50%.

It will be understood that, when an element is referred to as being "coupled" to another element, it can be directly coupled to the other element or intervening elements may be present. In contrast, when an element is referred to as being "directly coupled" to another element, there are no intervening elements present.

Likewise, it will be understood that, when an element is referred to as being "on" another element, it can be directly abutting the other element or intervening elements may be present. In contrast, when an element is referred to as being "directly on" to another element, there are no intervening elements present.

Spatially relative terms, such as "above", "below", "upper", "lower" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly. Well-known functions or constructions may not be described in detail for brevity and/or clarity.

Embodiments of the invention are described herein with reference to schematic illustrations of idealized embodiments of the invention. As such, variations from the shapes and relative sizes of the illustrations as a result, for example, of manufacturing techniques and/or tolerances, are to be expected. Thus, embodiments of the invention should not be construed as limited to the particular shapes and relative sizes of regions illustrated herein but are to include deviations in shapes and/or relative sizes that result, for example, from different operational constraints and/or from manufacturing constraints. Thus, the elements illustrated in the figures are schematic in nature and their shapes are not intended to illustrate the actual shape of a region of a device and are not intended to limit the scope of the invention. The relative sizes of various portions of the illustrate structures may be exaggerated for ease of illustration and explanation.

Various embodiments of the present invention are directed to an EMFC apparatuses which may be sufficiently miniaturized so as to be hand-held or otherwise transportable. Some of the apparatus structure is defined in a substrate, such as a chip/wafer, which can be operated to provide rapid highly accurate flow cytometry analysis from a small volume fluid sample. Various embodiments are described herein in the context of flow cytometers that are configured as a functional laboratory-on-a-chip, where the chip may be formed from various types of substrates. Moreover, some embodiments are described herein in the context of using flow cytometers to analyze cells within a blood sample; however, the invention is not limited thereto and may be applied much more broadly for analyzing any type of particles within fluid.

Some embodiments provide a miniaturized flow cytometer that regulates fluid transport through microchannels defined in a chip. Such chips may include a particle-counting structure and an optical-characterization and particle-sorting structure. Fluid may be transported through the microchannels using electric fields that generate electrokinetic forces on the fluid. This electrokinetic microfluidic flow can avoid the need for an external pump, valves and piping system, and enable the flow cytometer to be sufficiently miniaturized so as to be easily transportable and even made handheld.

When a solid surface is in contact with an aqueous solution, electrostatic charge will be established along the surface. These surface charges in turn attract the counter ions in the liquid to a region close to the solid-liquid interface which forms an electrical double layer (EDL). In the electrical double layer region, there are excess counter ions (net charge). When an external electrical field is applied tangentially to the solid surface, the excess counter ions will move under the influence of the applied electrical field, pulling the liquid with them and resulting in electroosmotic flow. The liquid movement is carried through to the rest of the liquid in the microchannel by viscous effects. In contrast, pumping a liquid through a small microchannel requires applying a very large pressure difference depending on the flow rate, and such pumping may not be possible for microchannel fluid flow because of the limited size and mechanical strength of microfluidic devices. Electroosmotic flow however can generate desired fluid flow rates in very small microchannels without any externally applied pressure difference by controlling the applied electrical fields via electrodes are inserted in different wells at the ends of the microchannels. Electroosmotic flow can thereby be used to transport liquids through the microchannels without employing external mechanical pumps, tubing and valves. The fluid flow rate can be controlling by regulating strength of the applied electrical fields.

Electrophoresis is the motion of a charged particle relative to the surrounding liquid under an applied electrical field. In a microchannel, the net velocity of a charged particle is determined by the electroosmotic velocity of the liquid and the electrophoretic velocity of the particle. If the surface charge of the particle is not strong or the ionic concentration of the liquid (e.g., typical buffer solutions) is high, the particle will move with the liquid. Using electrical fields to manipulate and transport biological cells in microchannels is particularly suitable for various embodiments of the present invention to provide a functional laboratory-on-a-chip.

According to various embodiments of the present invention, a handheld/transportable flow cytometer lab-on-a-chip device can include an EMFC chip, a differential electric resistive pulse sensor configured to count particles (e.g., blood cells, etc.) within a fluid sample, a miniaturized optical-characterization apparatus configured to detect one or more optical characteristics of the particles and to count numbers of different defined types of particles (e.g., by detecting specific fluorescent dye labels on the particles), an operation control circuit and a display unit.

EMFC apparatuses of the present invention may comprise, consist essentially of or consists of a substrate, a particle-sensing gate that reduces the cross-sectional area of a portion of the microchannel, a pair of signal- and noise-detection electrodes and a particle-detection circuit electrically connected to the signal- and noise-detection electrodes.

EMFC apparatuses of the present invention may comprise any suitable substrate, including but not limited to, substrates comprising glass and/or one or more polymers (e.g., polydimethylsiloxane). In some embodiments, the substrate is a laminate comprising two or more layers (e.g., an etched polydimethylsiloxane layer on a glass slide). As will be understood by those skilled in the art, intricate port/microchannel patterns may be formed in such substrates using standard lithography devices/methods. See, e.g., U.S. Pat. No. 8,188,438. Because the substrate can be manufactured using readily available materials and standard techniques, EMFC apparatuses of the present invention may be produced relatively inexpensively and may therefore be designed for disposable, single-use applications.

EMFC apparatuses of the present invention may comprise any suitable network of ports and microchannels. In some embodiments, the substrate comprises, consists essentially of or consists of an input port, an output port and a microchannel that connects the input port and the output port to allow a particle-carrying fluid to flow from the input port to the output port. In some embodiments, the output port comprises a plurality of particle-sorting output ports. Unlike the substrates described in U.S. Pat. No. 8,188,438, substrates of the present invention do not comprise signal- and noise-reduction channels extending away from the microchannel.

Figure 2:
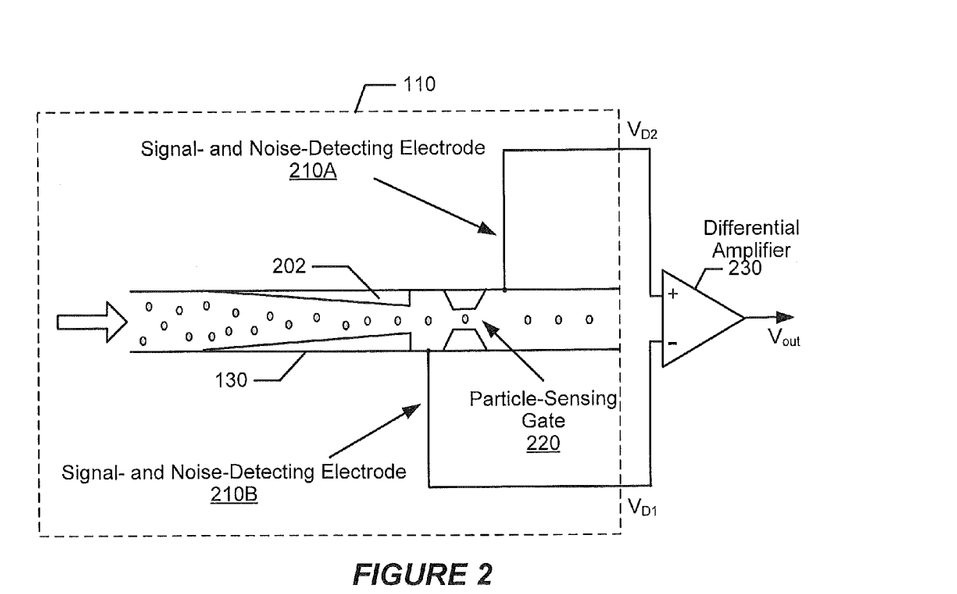
FIG. 2 is schematic diagram of a particle-counting sensor according to some embodiments of the present invention.
Figure 3:
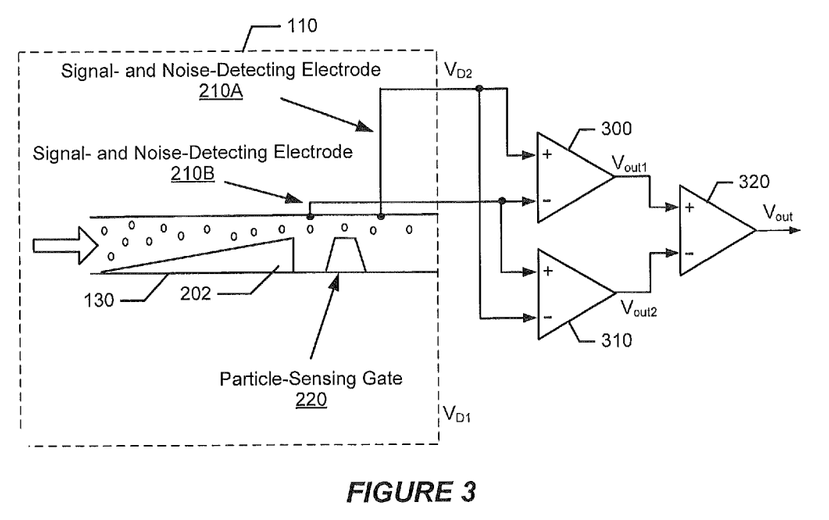
FIG. 3 is schematic diagram of a particle-counting sensor according to some embodiments of the present invention.
Figure 4:
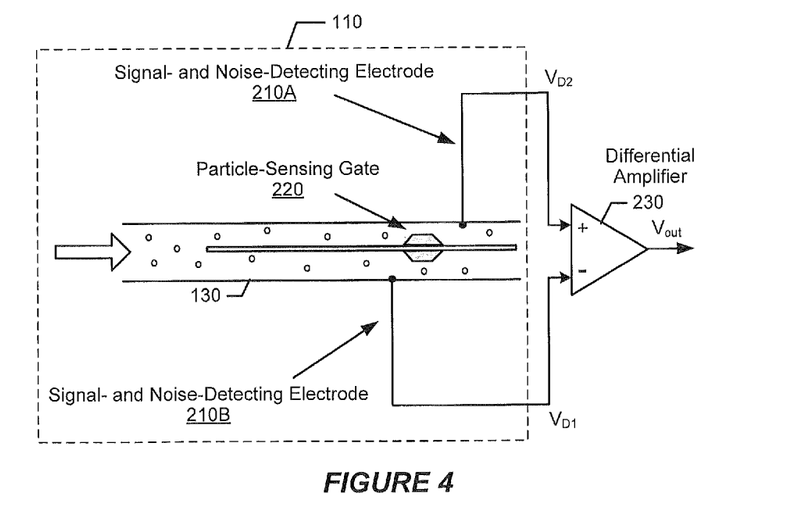
FIG. 4 is schematic diagram of a particle-counting sensor according to some embodiments of the present invention.

EMFC apparatuses of the present invention may comprise any suitable particle-sensing gate, including, but not limited to, particle-sensing gates as described in U.S. Pat. No. 8,188,438. In some embodiments, the particle-sensing gate comprises two or more members that extend toward each other from opposing surfaces of the microchannel (as shown in FIGS. 2-3), thereby reducing the cross-sectional area of the microchannel. In some embodiments, the particle-sensing gate comprises a member that extends from one sidewall of the microchannel toward the opposing sidewall (as shown in FIG. 3), thereby reducing the cross-sectional area of the microchannel. In some embodiments, the particle-sensing gate comprises a member that extends from a central region of the microchannel toward opposing sidewalls of the microchannel (as shown in FIG. 4), thereby reducing the cross-sectional area of the microchannel. In some embodiments, the particle-sensing gate reduces the cross-sectional area of the microchannel to less than about two, three, four, five, six, seven, eight, nine or ten times a cross-sectional area of one or more of the particles to be sensed (e.g., the maximum cross-sectional area of the particle). In some embodiments, the particle-sensing gate reduces the width of the microchannel to less than about two, three, four, five, six, seven, eight, nine or ten times the width of one or more of the particles to be sensed (e.g., the maximum width of the particle). In some embodiments, the particle-sensing gate has a cross-sectional gap size of about 1 µm to about 50 µm. In some embodiments, the particle-sensing gate has a cross-sectional gap size of about 0.1 µm to about 5 µm. In some embodiments, the particle-sensing gate has a length of about 5 µm to about 100 µm. As will be understood by those skilled in the art, reducing the cross-sectional area of the microchannel may increase the sensitivity of the particle-detection circuit to resistivity changes that occur as particles pass through the particle-sensing gate.

EMFC apparatuses of the present invention may comprise any suitable signal- and noise-detection electrodes, including, but not limited to, thin films electrodes. In some embodiments, the each of the signal- and noise-detection electrodes is a thin film electrode.

Signal- and noise-detection electrodes may be mounted in/on any suitable surface of the microchannel. In some embodiments, one or both of the signal- and noise-detection electrodes is embedded in a surface of the microchannel. In some embodiments, one or both of the signal- and noise-detection electrodes is mounted on a surface of the microchannel. In some embodiments, one or both of the signal- and noise-detection electrodes is mounted in/on a sidewall of the microchannel. In some embodiments, one or both of the signal- and noise-detection electrodes is mounted on the bottom surface of the microchannel. In some embodiments, one or both of the signal- and noise-detection electrodes is mounted on the top surface of the microchannel. In some embodiments, the signal- and noise-detection electrodes are mounted in/on the same surface of the microchannel (e.g., in/on the same sidewall of the microchannel). In some embodiments, the signal- and noise-detecting electrodes are mounted on different surfaces of the microchannel (e.g., opposing sidewalls of the microchannel).

Signal- and noise-detection electrodes may be recessed into, flush with or protruding from the surface of a microchannel. In some embodiments, one or both of the signal-and noise-detection electrodes is mounted flush with a surface of the microchannel. In some embodiments, one or both of the signal-and noise-detection electrodes protrudes from a surface of the microchannel (by about 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50 µm or more, for example).

Signal- and noise-detection electrodes may be positioned in any suitable portion of the microchannel so long as one of the signal and noise electrodes is positioned upstream of the particle-sensing gate and the other signal- and noise-detection electrode is positioned downstream of the particle-sensing gate. In some embodiments, one or both of the signal- and noise-detection electrodes is positioned within about 5, 10, 15, 20, 35, 30, 40, 50, 60, 70, 80, 90, 100, 120, 140, 160, 180, 200, 220, 240, 260, 280 or 300 µm of the particle-sensing gate. In some embodiments, the cross-sectional area of the particle-sensing gate and one or both of the signal- and noise-detection electrodes is less than about two, three, four, five, six, seven, eight, nine or ten times the cross-sectional area of one or more of the particles to be sensed (e.g., the maximum cross-sectional area of the particle). In some embodiments, the distance between the particle-sensing gate and one or both of the signal- and noise-detection electrodes is less than about two, three, four, five, six, seven, eight, nine or ten times the width of one or more of the particles to be sensed (e.g., the maximum width of the particle). In some embodiments, the signal- and noise-detection electrodes are positioned at the same or substantially the same distance away from the particle-sensing gate (e.g., equidistant or substantially equidistant from the transverse axis of the particle-sensing gate).

Signal- and noise-detection electrodes may be directly or indirectly coupled to particle-carrying fluid in the microchannel. In some embodiments, at least one of the signal- and noise-detection electrodes is mounted in/on a surface of the microchannel such that it may directly contact particle-carrying fluid in the microchannel. In some embodiments, at least one of the signal- and noise-detection electrodes is mounted in/on a reference channel that contains a fluid that is electrically coupled to the particle-containing fluid in the microchannel (e.g., a reference channel that contains the same buffer solution as the microchannel and that experiences the same electroosmotic flow as the microchannel). In some embodiments, at least one of the signal- and noise-detection electrodes is mounted in/on a reference channel that contains a fluid that is electrically isolated from the particle-containing fluid in the microchannel but is under the same electrokinetic force as the particle-containing fluid in the microchannel (e.g., a reference channel that contains the same buffer solution as the microchannel and that experiences the same electroosmotic flow as the microchannel). In some such embodiments, the microchannel and the reference channel are adjacent one another in a single EMFC chip.

EMFC apparatuses of the present invention may comprise any suitable particle-detection circuit, including, but not limited to, particle-detection circuits as described in U.S. Pat. No. 8,188,438. In some embodiments, the particle-detection circuit is configured to generate a particle-detection signal responsive to a differential voltage across the signal- and noise-detection electrodes, wherein the differential voltage across the signal- and noise-detection electrodes tracks changes in resistivity across the particle-sensing gate as particles in the particle-carrying fluid pass through the particle-sensing gate. The particle-detection circuit may be configured to cancel all or substantially all of the ambient electrical noise received by the signal- and noise-detection electrodes.

Electroosmotic flow between the input port and the output port may be generated by applying a voltage across an electrode positioned within the input port and an electrode positioned within the output port.

EMFC apparatuses of the present invention may comprise any suitable flow-focusing guide, including, but not limited to, flow-focusing guides as described in U.S. Pat. No. 8,188,438. In some embodiments, the flow-focusing guide has a cross-sectional fluid flow area along the flow direction of the microchannel that restricts particles flowing therethrough to exiting one at a time in a single line. In some embodiments, the flow-focusing guide comprises a step-wise converging section that generates a non-uniform electric field, which forces the particles in the particle-carrying fluid toward the center line of the microchannel, when a direct current is applied along the flow direction of the microchannel. See, c.f, Kang et al., ELECTROPHORESIS 27:694 (2006). In some embodiments, the upstream signal- and noise-reducing electrode serves as a flow-focusing guide (or some portion thereof). For example, in some embodiments, the upstream signal- and noise-detection electrode protrudes from a sidewall of the microchannel and repels particles having the same polarity as the electrode such that they are forced toward the center line of the microchannel.

EMFC apparatuses of the present invention may comprise any suitable particle-counting apparatus, including, but not limited to, particle-counting apparatuses as described in U.S. Pat. No. 8,188,438. In some embodiments, the particle-counting apparatus comprises, consists essentially of or consists of a particle-counting circuit configured to count individual particles as they pass through the particle-sensing gate (by counting the number of particle-detection signals generated by the particle-detection circuit, for example).

EMFC apparatuses of the present invention may comprise any suitable optical-characterization apparatus, including, but not limited to, optical-characterization apparatuses as described in U.S. Pat. No. 8,188,438. In some embodiments, the optical-characterization apparatus comprises, consists essentially of or consists of one or more light sources, one or more primary photodetectors, a reference photodetector and one or more comparator circuits. Each light source is configured to emit light to illuminate one or more optical-detection regions of the microchannel. Each primary photodetector may be configured to detect one or more wavelengths of light emitted by particles as they pass through an optical-detection region of the microchannel and to generate an output signal responsive thereto. The reference photodetector may be configured to generate a reference noise signal that is not responsive to light emitted by particles as they pass through the optical-detection region of the microchannel and that is characteristic of a noise component in one or more output signals generated by the primary photodetector(s). Each comparator circuit may be configured to generate a particle-characterization signal responsive to the difference(s) between the reference noise signal and the output signal(s) generated by the primary photodetector(s). The particle-characterization signal generated by the comparator circuit may be free or substantially free of the noise component(s) of the output signal(s). Accordingly, in some embodiments, the optical-characterization apparatus comprises, consists essentially of or consists of a first primary photodetector configured to detect light of a certain wavelength (or set of wavelengths) emitted by particles as they pass through the optical-detection region of the microchannel and to generate a first output signal responsive thereto, a second primary photodetector configured to detect light of a different wavelength (or set of wavelengths) emitted by particles as they pass through the optical-detection region of the microchannel and to generate a second output signal responsive thereto, a reference photodetector configured to generate a reference noise signal that is not responsive to light emitted by particles as they pass through the optical-detection region of the microchannel and that is characteristic of a noise component in the first and second output signals, a first comparator circuit configured to generate a first particle-characterization signal responsive to a difference between the first output signal and the reference noise signal so that the first particle-characterization signal is at least substantially free of the noise component from the first output signal and a second comparator circuit configured to generate a second particle-characterization signal responsive to a difference between the second output signal and the reference noise signal so that the second particle-characterization signal is at least substantially free of the noise component from the second output signal. Similarly, in some embodiments, the optical-characterization apparatus comprises a first primary photodetector configured to detect light of a certain wavelength (or set of wavelengths) emitted by particles as they pass through the optical-detection region of the microchannel and to generate a first output signal responsive thereto, a second primary photodetector configured to detect light of a different wavelength (or set of wavelengths) emitted by particles as they pass through the optical-detection region of the microchannel and to generate a second output signal responsive thereto, a-reference photodetector configured to generate a reference noise signal that is not responsive to light emitted by particles as they pass through the optical-detection region of the microchannel and that is characteristic of a noise component in the first and second output signals and a comparator circuit configured to generate first and second particle-characterization signals responsive to differences between the reference noise signal and the first and second output signals, respectively, so that the first and second particle-characterization signal are at least substantially free of the noise components from the first and second output signals.

Optical-characterization apparatuses of the present invention may be configured to utilize any suitable number of wavelengths to characterize particles as they pass through the optical-detection region(s) of the EMFC chip 100. In addition to utilizing light sources capable of emitting multiple wavelengths of light, the number of wavelengths utilized may be increased by including multiple optical-detection regions in the same microchannel. For example, in some embodiments of the present invention, the optical-characterization apparatus is configured to characterize particles as they pass through two or more optical-detection regions, each associated with a light source configured to emit light of two specific wavelength (or sets of wavelengths) and two primary photodetectors, each configured to detect one of the specific wavelengths (or sets of wavelengths) of light emitted by the light source and to generate an output signal responsive thereto.

Optical-characterization apparatuses of the present invention may comprise any suitable light source, including, but not limited to, light sources as described in U.S. Pat. No. 8,188,438. In some embodiments, the light source comprises, consists essentially of or consists of a light emitting diode. In some embodiments, the light source comprises a collimator and/or one or more optic filters. The light source may be configured to emit light of any suitable wavelength(s) and to illuminate any suitable portion(s) of the microchannel. In some embodiments, the light source is configured to emit multiple wavelengths of light. For example, the light source may be a laser or light emitting diode configured to generate red light having a wavelength of about 635 nm and blue light having a wavelength of about 488 nm.

EMFC apparatuses of the present invention may comprise any suitable particle-sorting apparatus, including, but limited to, particle-sorting apparatuses as described in U.S. Pat. No. 8,188,438. In some embodiments, the particle-sorting apparatus comprises, consists essentially of or consists of a particle-sorting circuit configured to separately and selectively control the electroosmotic flow between an optical-detection region of the microchannel and two or more particle-sorting output ports such that individual particles may be selectively transported to one of the particle-sorting outputs responsive to the optical characteristic(s) thereof.

In some embodiments, two or more of the apparatuses described above are combined to form a single apparatus. For example, in some embodiments, the EMFC apparatus comprises an optical-characterization and particle-sorting apparatus configured to detect one or more optical characteristics of each particle that passes through an optical-detection region of the microchannel and to sort the particles responsive to the optical characteristics detected.

Figure 1:
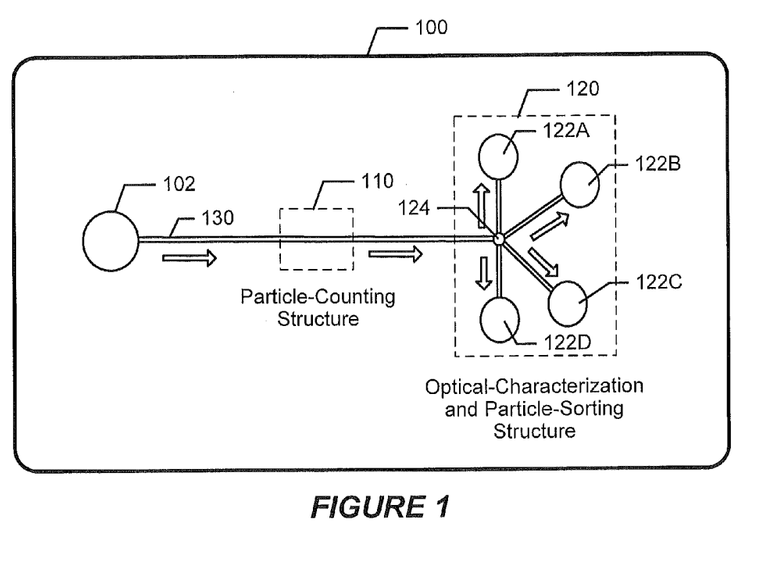
FIG. 1 is a plan view of an EMFC chip according to some embodiments of the present invention.

As shown in FIG. 1, in some embodiments of the present invention, the EMFC apparatus is an EMFC chip 100 comprising an input port 102, a particle-counting sensor 110, an optical-characterization and particle-sorting structure 120 and a microchannel 130 that allows fluid to flow therebetween. The input port 102 comprises a reservoir configured to hold a sample solution (e.g., a buffer solution containing a blood sample). The particle-counting sensor 110 is configured to detect and/or count particles in the sample solution using a microfluidic differential electrical resistance pulse sensor. The optical-characterization and particle-sorting structure 120 is configured to optically distinguish various types of particles as they pass through an optical-detection region 124 thereof and to sort those particles among a plurality of output ports 122A-D responsive to their optical characteristics.

The sample solution is moved via the microchannel 130 from the input port 102 through the particle-counting sensor 110 and then through the optical-characterization and particle-sorting structure 120 by applying an electric field along the microchannel 130 that creates an electrokinetic force on the sample solution. Further electric fields between the optical-detection region 124 and output ports 122A-D are generated and selectively controlled to sort the particles in the sample solution. As will be explained in further detail below with regard to FIG. 7, a miniaturized optical system may be configured to detect and classify the optical characteristics of particles passing through the optical-detection region 124. For example, blood cells may be labeled with certain fluorescent dyes that can be optically identified as the cells move through the optical-detection region 124.

In some embodiments, a plurality of particle-counting sensors 110 is positioned downstream of the optical-detection region 124, with at least one particle-counting sensor 110 positioned in each of the branched microchannel sorting pathways leading to output ports 122A-D. Such downstream particle-counting sensors 110 may be used in addition to or instead of the upstream particle-counting sensor 110 shown in FIG. 1 to count total particles passing through the branched microchannels.

As shown in FIGS. 2-4, in some embodiments of the present invention, the particle-counting sensor 110 comprises a flow-focusing guide 202, a particle-sensing gate 220 and a pair of signal- and noise-detection electrodes 210A-B. The flow-focusing guide 202 is positioned upstream of the particle-sensing gate 220 and the signal- and noise-detection electrodes 210A-B and causes the particles in the sample solution to pass through the particle-sensing gate 220 one at a time. The particle-sensing gate 220 reduces the cross-sectional area of a portion of the microchannel. In some embodiments, the particle-sensing gate 220 reduces the cross-sectional area of the microchannel to less than ten times the cross-sectional area of an individual particle as it passes through the particle-sensing gate 220. The signal- and noise-detection electrodes 210A-B are electrically connected to the microchannel 130 on either side of the particle-sensing gate 220 and are configured to sense resistivity changes as particles pass through the particle-sensing gate 220.

Also as shown in FIGS. 2-4, in some embodiments of the present invention, the particle-counting sensor 110 is electrically connected to a differential amplifier circuit configured to generate a particle-detection signal Vout in response to a differential voltage across the signal- and noise-detection electrodes 210A-B, wherein the differential voltage tracks changes in resistivity across particle-sensing gate 220 as individual particles pass therethrough.

As shown in FIGS. 2 and 4, in some embodiments, the differential amplifier circuit is a single-stage differential amplifier circuit that comprises a differential amplifier 230 that has two differential input terminals—with one terminal connected to the signal- and noise-detection electrode 210A positioned upstream of the particle-sensing gate 220 to sense a first input voltage $V_{D1}$ and the other terminal connected to the signal- and noise-detection electrode 210B positioned downstream of the particle-sensing gate 220 to sense a second input voltage $V_{D2}$—and that is configured to generate the particle-detection signal Vout responsive to a differential between the first and second input voltages $V_{D1}$, $V_{D2}$.

As shown in FIG. 3, in some embodiments, the differential amplifier circuit is a dual-stage differential amplifier circuit that comprises two first-stage differential amplifiers 300,310 and one second-stage differential amplifier 320. The first-stage differential amplifiers 300,310 are oppositely connected across the signal- and noise-detecting electrodes 210A-B and their respective output signals Vout1, Vout2 are differentially amplified by the second stage differential amplifier 320 to generate the particle-detection signal Vout. In some such embodiments, the signal- and noise-detection electrode 210A positioned upstream of the particle-sensing gate 220 is electrically connected to the negative input terminal of one first-stage differential amplifier 300 and to the positive input terminal of the other first-stage differential amplifier 310, while the signal- and noise-detection electrode 210B positioned downstream of the particle-sensing gate 220 is electrically connected to the positive input terminal of one first-stage differential amplifier 300 and to the negative input terminal of the other first-stage differential amplifier 310. Particles flowing through the particle-sensing gate 220 cause the first-stage differential amplifiers 500,510 to generate output signals Vout1, Vout2 having a reduced common ambient noise component which is further canceled by the second-stage differential amplifier 520, so that the particle-detection signal Vout is substantially free of the received ambient electrical noise.

Because the differential amplifier circuit generates the particle-detection signal Vout responsive to resistivity changes that occur across the particle-sensing gate 220 as particles flow through the particle-sensing gate 220 under an electric field applied along the microchannel 130, the electric field that is used to provide electrokinetic transport of the fluid and particles through the microchannel 130 may also be used to sense resistivity changes across the particle-sensing gate 220 as particles flow therethrough.

The particle-counting sensor 110 may further comprise a particle-counting circuit configured to count particles as they pass through the particle-sensing gate 220. In some such embodiments, the particle-counting circuit is configured to count particles by detecting electrical pulses in the particle-detection signal Vout.

Ambient electrical noise received by each of the signal- and noise-detection electrodes 210A-B may have similar characteristics because the signal- and noise-detection electrodes 210A-B are closely located and are connected to the same microchannel 130. The ambient electrical noise may arise from external sources, such as from adjacent electrical power systems which radiate 60 Hz or other frequency noise and/or from computers, cell phones, and other electronic devices that radiate in a frequency range from hundreds of Hz and GHz. The signal- and noise-detection electrodes 210A-B may be structurally similar/identical so that they receive similar/equal amounts of ambient electrical noise. Because the differential amplifier circuit responds to a differential voltage across the signal- and noise-detection electrodes 210A-B, it can substantially or totally cancel a common component of the ambient electrical noise received by the signal- and noise-detection electrodes 210A-B as it generates the particle-detection signal Vout.

When a particle passes through the particle-sensing gate 220, a differential voltage is generated across the signal- and noise-detection electrodes 210A-B which is sensed and amplified by the differential amplifier circuit. Although the differential voltage appearing across the input terminals of the differential amplifier circuit may have a relatively small amplitude, the amplitude of the differential voltage can be substantially enlarged by the gain of the differential amplifier circuit. Accordingly, particle-counting apparatuses 110 of the present invention may therefore provide a significant improvement in both sensitivity and signal-to-noise ratio in the detection of fluid-borne particles.

Figure 5:
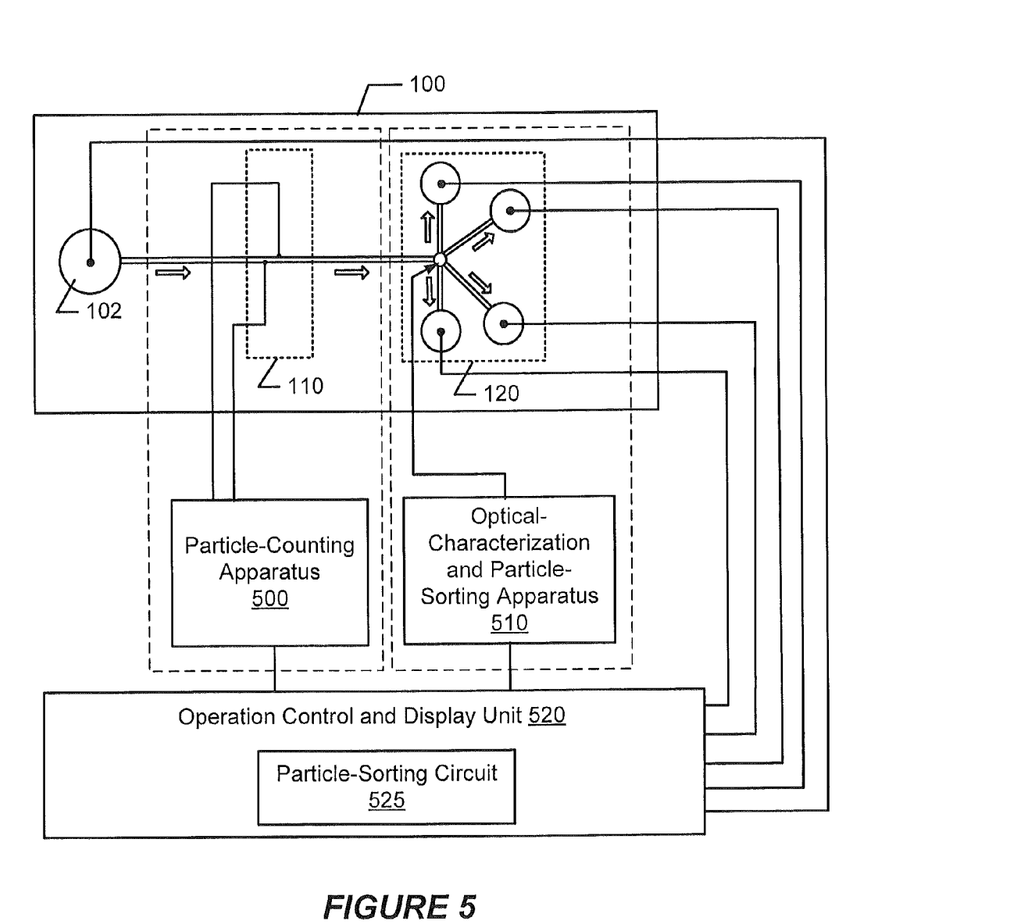
FIG. 5 is a plan view of an EMFC apparatus according to some embodiments of the present invention.

As shown in FIG. 5, in some embodiments of the present invention, the EMFC apparatus comprises an EMFC chip 100, a particle-counting apparatus 500, an optical-characterization and particle-sorting apparatus 510 and, an operation control and display unit 520 comprising a particle-sorting circuit 525. The particle-counting apparatus 500 is configured to count particles as they pass through the particle-counting sensor 110. The optical-characterization and particle-sorting apparatus 510 is configured to generate particle-classification signals based upon the optical characteristics of the light emitted by particles passing through one or more optical-detection regions of the EMFC chip 100. The operation control and display unit 520 is configured to separately and selectively control electroosmotic flow between the optical-detection region of the EMFC chip 100 and the particle-sorting output ports such that individual particles may be selectively transported to one of the particle-sorting outputs responsive to the particle-characterization signals generated by the optical-characterization and particle-sorting apparatus 510.

The EMFC chip 100 may be an EMFC chip as described above with respect to any one of FIGS. 1-4.

The particle-counting apparatus 500 may comprise a single- or double-stage differential amplifier circuit as described above with respect to FIGS. 2-4 and a particle-counting circuit configured to count particles by detecting electrical pulses in the particle-detection signal Vout. The particle-counting apparatus 500 may count pulses in the particle-detection signal Vout or may provide the particle-detection signal Vout to the control unit 520 for counting.

The optical-characterization and particle-sorting apparatus 510 may comprise one or more light sources (e.g., a plurality of light emitting diodes), each configured to emit one or more wavelengths of light to illuminate an optical-detection region of the microchannel; one or more primary photodetectors (e.g., a pair of primary photodetectors for each light source), each configured to detect one or more wavelengths of light emitted by particles as they pass through an optical-detection region of the microchannel and to generate an output signal responsive thereto; a reference photodetector configured to generate a reference noise signal that is not responsive to light emitted by particles as they pass through the optical-detection region and that is characteristic of the noise component(s) in the output signal(s) generated by the primary photodetector(s); and one or more comparator circuits, each configured to generate a particle-characterization signal responsive to the differences between the reference noise signal and output signals generated by the primary photodetector(s). The particle-characterization signals generated by the comparator circuit may be free or substantially free of the noise component(s) of the output signal(s).

Figure 6:
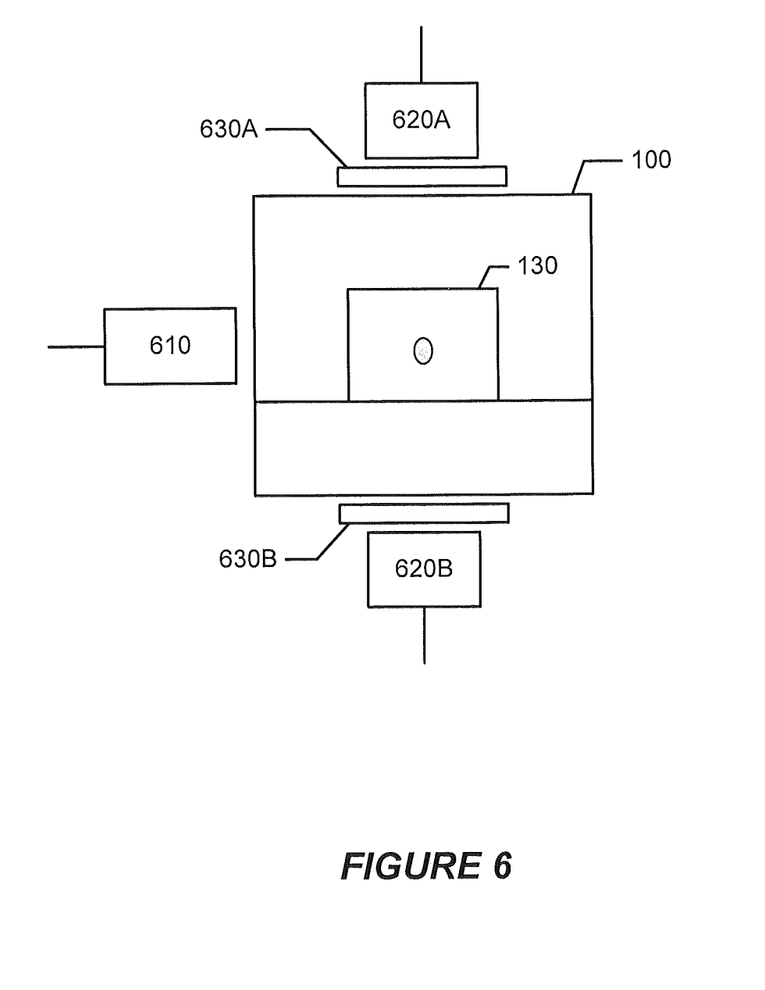
FIG. 6 is a cross-sectional schematic diagram of an optical-detection region of microchannel according to some embodiments of the present invention.

The light source(s) and primary photodetector(s) may be positioned in any suitable locations. As shown in FIG. 6, in some embodiments of the present invention, a light source 610 (e.g., a light emitting diode that emits light of two or more specific wavelengths (or sets of wavelengths) of light) is positioned adjacent to the EMFC chip 100 such that its light passes through one sidewall of the microchannel, through the microchannel itself and then out the opposing sidewall of the microchannel; a first primary photodetector 620A is positioned above the EMFC chip 100 such that it detects light emitted upward from particles in the microchannel; and a second primary photodetector 620B is positioned beneath the EMFC chip 100 such that it detects light emitted downward from particles in the microchannel.

The light source(s) and primary photodetector(s) may be positioned any suitable distance away from the microchannel. In some embodiments, one or more light source(s) and/or one or more primary photodetectors is positioned directly on the substrate. As shown in FIG. 6, in some embodiments, one or more optical filters 630A, 630B may be positioned between each of the photodetectors 620A, 620B and the substrate. Optical filters may likewise be positioned between the substrate and each light source.

The operation control and display unit 520 may comprise any suitable data acquisition, data processing and display apparatuses/circuits. As shown in FIG. 5, in some embodiments of the present invention, the operation control and display unit 520 comprises a particle-sorting circuit 525.

The operation control and display unit 520 is electrically connected to electrodes that are in contact with the input port 102 and each of the particle-sorting output port 122A-Ds.

The operation control and display unit 520 (and, more particularly, a particle-sorting circuit 525 therein) may be configured to separately and selectively control electroosmotic flow between the optical-detection region(s) of the EMFC chip 100 and the particle-sorting output ports 122A-D such that individual particles may be selectively transported to one of the particle-sorting outputs responsive to the particle-characterization signals generated by the optical-characterization and particle-sorting apparatus 510. For example, the particle-sorting circuit 525 may supply 50V, another voltage, or a time varying range of voltages, between the input port 102 and the first particle-sorting output port 122A to move a first detected type of particle from the optical-detection region(s) to the first output port 122A. When a second type of particle is detected by the optical-characterization and particle-sorting apparatus 510, the particle-sorting circuit 725 can supply the voltage between the input port 102 and the second particle-sorting output port 122B to move the particle to the second particle-sorting output port 122B. Similarly, the particle-sorting circuit 525 can selectively supply the voltage between the input port 102 and a selected one of the third and fourth particle-sorting output ports 122C-D to move a third type of particle and a fourth type of particle to the third particle-sorting output port 122C or the fourth particle-sorting output port 122D, respectively.

The operation control and display unit 520 may comprise any suitable display, including, but not limited to, liquid crystal displays.

The operation control and display unit 520 may display any suitable information and may be configured to display information in real time as the sample fluid is being analyzed.

The operation control and display unit 520 may be any type of data processing apparatus, including, but not limited to, a Personal Data Assistant, a cellular smart phone, a palmtop computer, a laptop computer and a desktop computer.

EMFC apparatuses of the present invention (e.g., EMFC apparatuses as describe above with respect to FIG. 5) may be used to detect, count and/or sort specific cell types in a fluid sample (e.g., the number of CD4+ cells in a blood sample).

Although EMFC apparatuses of the present invention may be configured to detect, count and sort any suitable cell type, in the interest of brevity, embodiments of the present invention will hereinafter be described with respect to the detection, counting and sorting of fluorescently dyed CD4+ cells in a blood sample.

As the fluorescently dyed CD4+ cells pass through the optical-detection region, a fluorescent signal (e.g., green light) is detected and a particle-characterization signal is sent to the operation control and display unit 520. The operation control and display unit 520 records the cell and modulates the electric field in the microchannel to transport the CD4+ cell to a selected one of the particle-sorting output ports 122A-D to be sorted or collected there. The control unit 520 may display on a display device an indication of the number of counted CD4+ cells, as determined by the optical-characterization and particle-sorting apparatus 510, and an indication of the total number of counted cells, as determined by the particle-counting apparatus 500, and/or it may display the percentage of CD4+ cells relative to other cells in the sample. This information can be used to detect a disease (e.g., HIV) and/or to characterize its progress.

Figure 7:
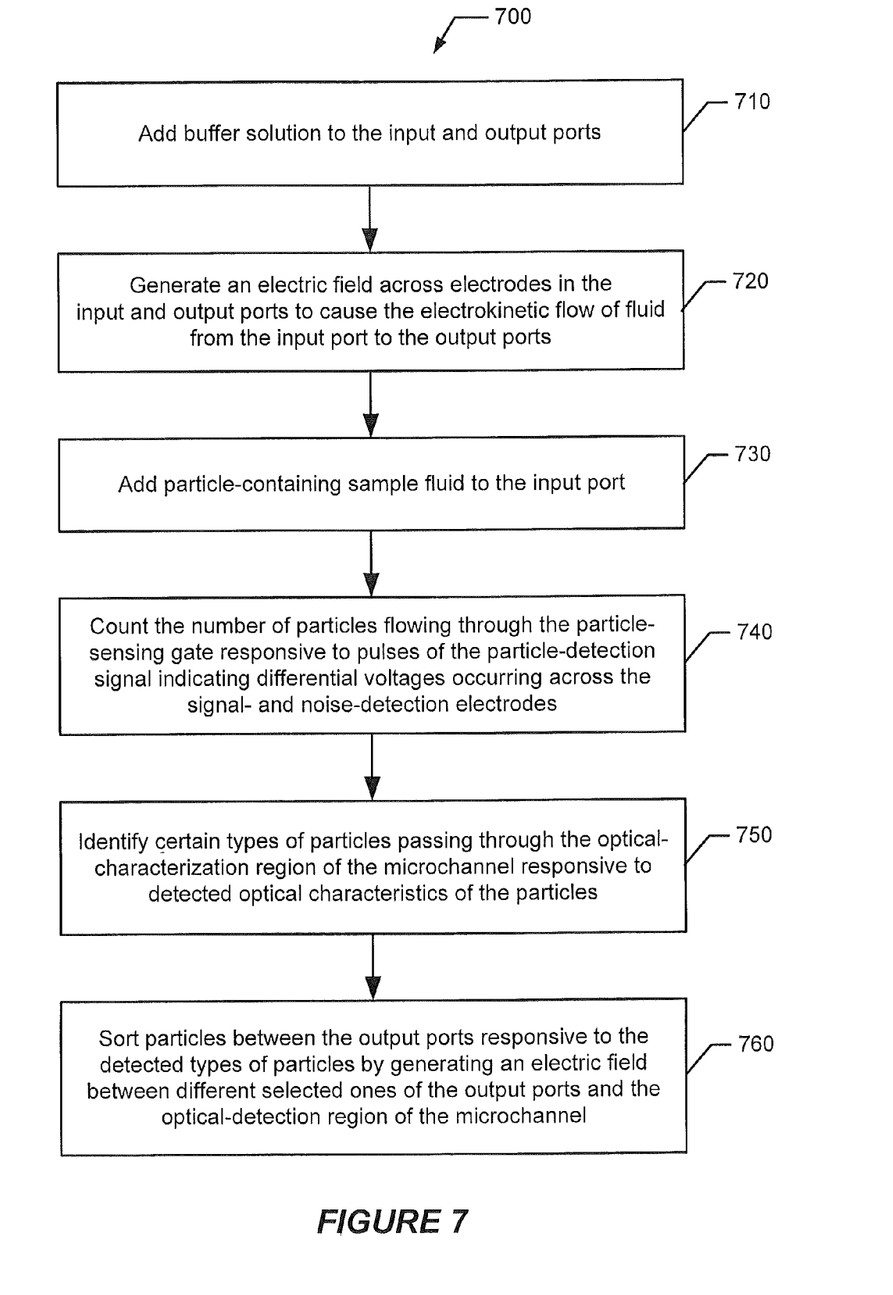
FIG. 7 is a flowchart that illustrates various operations that can be carried out using EMFC apparatuses of the present invention.

Exemplary operations that may be carried out to perform analysis of a fluid sample using EMFC apparatuses of the present invention are shown in the flowchart of FIG. 7. Referring to FIG. 7, an EMFC chip is placed in a chip-holding stage, which ensures precise alignment of the light source (e.g. an optical fiber or a light emitting diode) and the optical-detection region of the microchannel and of the electrodes and input/output ports. Buffer solution is added to the input and the particle-sorting output ports 710. An electric field is generated across electrodes in the input and output ports to cause electrokinetic flow of fluid from the input port to the output ports 720. A particle-containing sample fluid (e.g., a blood sample) is added to the input port 730. The number of particles flowing through the particle-sensing gate is counted responsive to pulses of the particle-detection signal, which indicate differential voltages occurring across the signal- and noise-detection electrodes 740. The types of particles passing through the optical-detection region of the microchannel are identified responsive to their optical characteristics 750. The particles are then sorted into the particle-sorting output ports responsive to their detected types by generating electric fields between different selected ones of the particle-sorting output ports and optical-detection region of the microchannel 760. As will be understood by those skilled in the art, one or more of the operations described above maybe performed by a microprocessor in an operation control and display unit (e.g., an operation control and display unit as described above with respect to FIG. 5).

Although the present invention has been described with reference to specific details of certain embodiments thereof, it is not intended that such details should be regarded as limitations upon the scope of the invention except as and to the extent that they are included in the accompanying claims. As noted above, the above-described embodiments can be modified or varied without departing from the present invention. It is therefore to be understood that, within the scope of the claims and their equivalents, the present invention can be practiced otherwise than as specifically described above.

That which is claimed is:

1. An electrokinetic microfluidic flow cytometer apparatus, comprising:
 a substrate having defined therein an input port, an output port, and a microchannel that fluidly connects the input port and the output port to allow a particle-carrying fluid to flow therebetween;
 a particle-sensing gate that reduces the cross-sectional area of a portion of the microchannel;
 a pair of signal- and noise-detection electrodes, each mounted in or on a surface of the microchannel; and
 a particle-detection circuit electrically connected to the signal- and noise-detection electrodes,
 wherein one of the signal- and noise-detection electrodes is positioned upstream of the particle-sensing gate and the other is positioned downstream of the particle-sensing gate, and
 wherein the particle-detection circuit is configured to generate a particle-detection signal responsive to changes in resistivity across the particle-sensing gate as particles flow through the particle-sensing gate, while at least substantially canceling a common component of ambient electrical noise received by the signal- and noise-detection electrodes.

2. The electrokinetic microfluidic flow cytometer apparatus of claim 1,
 wherein the distance between the particle-sensing gate and one or both of the signal- and noise-detection electrodes is less than about ten times a width of an individual particle as it flows through the microchannel.

3. The electrokinetic microfluidic flow cytometer apparatus of claim 1,
 wherein the distance between the particle-sensing gate and one or both of the signal- and noise-detection electrodes is about 1 µm to about 50 µm.

4. The electrokinetic microfluidic flow cytometer apparatus of claim 1,
 wherein the signal- and noise-reduction electrodes are substantially equidistant from the particle-sensing gate.

5. The electrokinetic microfluidic flow cytometer apparatus of claim 1,
 wherein the distance between the particle-sensing gate and the upstream signal- and noise-detection electrode is at least about 5 µm different than the distance between the particle-sensing gate and the downstream signal- and noise-detection electrode.

6. The electrokinetic microfluidic flow cytometer apparatus of claim 1,
 wherein at least one of the signal- and noise-detection electrodes is mounted in or on a sidewall of the microchannel.

7. The electrokinetic microfluidic flow cytometer apparatus of claim 1,
 wherein at least one of the signal- and noise-detection electrodes is mounted in or on a bottom surface of the microchannel.

8. The electrokinetic microfluidic flow cytometer apparatus of claim 1,
 wherein the signal- and noise-detection electrodes are mounted in or on the same surface of the microchannel.

9. The electrokinetic microfluidic flow cytometer apparatus of claim 1,
 wherein the signal- and noise-detection electrodes are mounted in or on opposing surfaces of the microchannel.

10. The electrokinetic microfluidic flow cytometer apparatus of claim 1,
 wherein one or both of the signal- and noise-detection electrodes protrudes into the microchannel.

11. The electrokinetic microfluidic flow cytometer apparatus of claim 1, further comprising:
 a flow-focusing guide having a converging cross-sectional fluid flow area along the flow direction with a cross-sectional fluid flow output area that restricts particles flowing therethrough to exiting one at a time,
 wherein the flow-focusing guide is positioned upstream of the signal- and noise-detection electrodes and the particle-sensing gate.

12. The electrokinetic microfluidic flow cytometer apparatus of claim 11,
 wherein the flow-focusing guide comprises a step-wise converging section that generates a non-uniform electric field, which forces particles in the particle-carrying fluid toward the center line of the microchannel, when a direct current is applied along the flow direction of the microchannel.

13. The electrokinetic microfluidic flow cytometer apparatus of claim 1,
 wherein the particle-detection circuit comprises a differential amplifier having a pair of input terminals, each connected to one of the signal- and noise-detection electrodes.

14. An electrokinetic microfluidic flow cytometer apparatus, comprising:
 a substrate having defined therein an input port, a plurality of particle-sorting output ports, and a microchannel that fluidly connects the input port and the plurality of particle-sorting output ports to allow a particle-carrying fluid to flow therebetween responsive to an electric field along the microchannel;
 a light source configured to emit at least two wavelengths of light to illuminate an optical-detection region of the microchannel;
 a first primary photodetector positioned above the substrate and configured to detect a first wavelength of light emitted from particles as they flow through the optical-detection region of the microchannel and to generate a first output signal responsive thereto, the first output signal containing a first noise component;
 a second primary photodetector positioned beneath the substrate and configured to detect a second wavelength of light emitted from particles as they flow through the optical-detection region of the microchannel and to generate a second output signal responsive thereto, the second output signal containing a second noise component;
 a reference photodetector configured to generate a reference noise signal that is not responsive to light emitted from particles as they flow through the optical-detection region and is characteristic of the first and second noise components; and
 a first comparator circuit configured to generate a first particle-characterization signal responsive to a difference between the first output signal and the reference noise signal so that the first particle-characterization signal is at least substantially free of the noise component from the first output signal; and
 a second comparator circuit configured to generate a second particle-characterization signal responsive to a difference between the second output signal and the reference noise signal so that the second particle-characterization signal is at least substantially free of the noise component from the second output signal.

15. The electrokinetic microfluidic flow cytometer apparatus of claim 14,
wherein the reference photodetector is configured to have substantially the same operational characteristics as the first and second primary photodetectors.

16. The electrokinetic microfluidic flow cytometer apparatus of claim 14, further comprising a source filter between the light source and the substrate.

17. The electrokinetic microfluidic flow cytometer apparatus of claim 14, further comprising a first optical filter between the first primary photodetector and the substrate.

18. The electrokinetic microfluidic flow cytometer apparatus of claim 14, further comprising a second optical filter between the second primary photodetector and the substrate.

19. The electrokinetic microfluidic flow cytometer apparatus of claim 14, further comprising:
a control circuit configured to classify particles responsive to the first and second particle-characterization signals.

20. The electrokinetic microfluidic flow cytometer apparatus of claim 19,
wherein the first comparator circuit comprises a first differential amplifier having a pair of input terminals, with one of the input terminals connected to receive the first output signal from the first primary photodetector and the other input terminal connected to receive the reference noise signal from the reference photodetector,
wherein the first differential amplifier is configured to generate the first particle-characterization signal responsive to a voltage difference between the input terminals that indicates a detected optical characteristic of a particle within the optical-detection region responsive to illumination by the at least one wavelength of light,
wherein the second comparator circuit comprises a second differential amplifier having a pair of input terminals, with one of the input terminals connected to receive the second output signal from the second primary photodetector and the other input terminal connected to receive the reference noise signal from the reference photodetector, and
wherein the second differential amplifier is configured to generate the second particle-characterization signal responsive to a voltage difference between the input terminals that indicates a detected optical characteristic of a particle within the optical-detection region responsive to illumination by the at least one wavelength of light emitted by the light source.

21. The electrokinetic microfluidic flow cytometer apparatus of claim 14,
wherein the first particle-characterization signal indicates when particles flowing through the optical-detection region emit green light responsive to illumination of the optical-detection region, and
wherein the second particle-characterization signal indicates when particles flowing through the optical-detection region emit red light responsive to illumination of the optical-detection region.

22. The electrokinetic microfluidic flow cytometer apparatus of claim 14, further comprising:
a particle-sorting circuit configured to separately and selectively control voltages applied between the optical-detection region of the microchannel and each of the particle-sorting output ports such that each individual particle is selectively transported to one of the particle-sorting outputs responsive to the first particle-characterization signal and/or the second particle-characterization signals.

23. The electrokinetic microfluidic flow cytometer apparatus of claim 14,
wherein the particle-carrying fluid comprises a plurality of different types of blood cells,
wherein at least one of the different types of blood cells is labeled with a fluorescent dye that emits the first wavelength of light responsive to illumination with the at least one wavelength of light emitted by the light source,
wherein at least one other of the different types of blood cells is labeled with a fluorescent dye that emits the second wavelength of light responsive to illumination with the at least one wavelength of light emitted by the light source.

24. The electrokinetic microfluidic flow cytometer apparatus of claim 23, wherein the first comparator circuit comprises a first differential amplifier having a pair of input terminals, with one of the input terminals connected to receive the first output signal from the first primary photodetector and the other input terminal connected to receive the reference noise signal from the reference photodetector,
wherein the first differential amplifier is configured to generate the first particle-characterization signal responsive to a voltage difference between the input terminals that indicates a detected optical characteristic of a particle within the optical-detection region responsive to illumination by the at least one wavelength of light,
wherein the second comparator circuit comprises a second differential amplifier having a pair of input terminals, with one of the input terminals connected to receive the second output signal from the second primary photodetector and the other input terminal connected to receive the reference noise signal from the reference photodetector, and
wherein the second differential amplifier is configured to generate the second particle-characterization signal responsive to a voltage difference between the input terminals that indicates a detected optical characteristic of a particle within the optical-detection region responsive to illumination by the at least one wavelength of light.

25. The electrokinetic microfluidic flow cytometer apparatus of claim 23,
wherein the first particle-characterization signal indicates that a first type of blood cell is present in the optical-detection region of the microchannel, and
wherein the second particle-characterization signal indicates that a second type of blood cell is present in the optical-detection region of the microchannel.

26. The electrokinetic microfluidic flow cytometer apparatus of claim 25, further comprising:
a particle-sorting circuit configured to separately and selectively control voltages applied between the optical-detection region of the microchannel and each of the particle-sorting output ports such that the first type of blood cell is transported to one of the particle-sorting outputs and the second type of blood cell is transported to one other of the particle-sorting outputs.

* * * * *